United States Patent

Morita et al.

[11] Patent Number: 5,614,311
[45] Date of Patent: Mar. 25, 1997

[54] ADHESIVE TAPE

[75] Inventors: Yasuhiko Morita; Toshiaki Masuda, both of Osaka, Japan

[73] Assignee: Nissho Corporation, Osaka, Japan

[21] Appl. No.: 455,518

[22] Filed: May 31, 1995

[30] Foreign Application Priority Data

Jul. 1, 1994 [JP] Japan ................... 6-173207

[51] Int. Cl.$^6$ ..................................... C09J 7/02
[52] U.S. Cl. ........................... 428/317.3; 428/354
[58] Field of Search ..................... 428/343, 354, 428/317.3

[56] References Cited

FOREIGN PATENT DOCUMENTS

| | | |
|---|---|---|
| 2-115239 | 4/1990 | Japan . |
| 4-79662 | 12/1992 | Japan . |
| 6-31825 | 2/1994 | Japan . |
| 6-39140 | 5/1994 | Japan . |
| WO89/04253 | 5/1989 | WIPO . |

*Primary Examiner*—Jenna Davis
*Attorney, Agent, or Firm*—Armstrong, Westerman, Hattori, McLeland & Naughton

[57] ABSTRACT

An adhesive tape comprising a water impermeable, gas permeable tape substrate, a pressure-sensitive adhesive layer provided on one side of the tape substrate, and a porous sheet provided on a portion of the pressure-sensitive adhesive layer, the porous sheet being capable of expanding to have an apparent density of 0.01 to 0.20 g/cm$^3$ when absorbing water to saturation. The adhesive tape prevents the accumulation of perspiration between the adhesive tape and the skin of a user on which the adhesive tape is being applied and, hence, is not readily peeled off from the skin. The porous sheet expands upon absorbing blood from a wound to press against the wound, resulting in an enhanced hemostasis effect.

4 Claims, 1 Drawing Sheet

ADHESIVE TAPE

BACKGROUND OF THE INVENTION

The present invention relates to an adhesive tape for covering a wound or the like. More particularly, the present invention relates to an adhesive tape most suitable for stopping bleeding from a wound (hereinafter referred to as "hemostasis adhesive tape").

Heretofore, there has been known a hemostasis adhesive tape using a substrate having a large elasticity, with which a wound is pressed to prevent bleeding from the wound. However, the pressure applied to the skin by use of only such a substrate having a large elasticity is small, resulting in an insufficient hemostasis effect.

Aside from such improvement on the substrate, an adhesive tape using a pad composed of an elastic material has been developed. With use of this adhesive tape, the pressure applied to the skin is also insufficient.

Accordingly, there has been a strong demand for development of an adhesive tape which is capable of strongly pressing against a wound to produce a sufficient hemostasis effect. In compliance with this demand, an adhesive tape using as a pad a sheet composed of an absorbent material has been developed.

With use of this adhesive tape, the sheet composed of the absorbent material absorbs blood from a wound to swell, thereby pressing against the wound to produce a hemostasis effect. However, this adhesive tape involves a sanitary problem that additives contained in the absorbent material come into direct contact with the wound.

Japanese Examined Utility Model Publication No. 6816/1994 proposes, as an adhesive tape wherein such problem is solved, one using a pad produced by mechanically compressing a nonwoven fabric, which pad expands upon contacting blood, thereby pressing against the wound to stop bleeding.

However, all of the above-mentioned adhesive tapes have a drawback that they are prone to be peeled off from the skin when the skin perspires. When a user having such adhesive tape applied on its skin takes a bath, the adhesive tape is peeled off because of this drawback. For this reason, a patient who is being subjected to dialysis treatment cannot take a bath soon after the adhesive tape is applied to the portion of the patient where a needle for dialysis is extracted after termination of a dialysis operation.

It is an object of the present invention to provide an adhesive tape which can prevent the accumulation of perspiration between the adhesive tape and the skin of a user on which the adhesive tape is being applied and, hence, is not readily peeled off from the skin.

Another object of the present invention is to provide an adhesive tape which, even when a user applies the adhesive tape to a bleeding wound on its own skin and thereafter takes a bath, is not peeled off from the skin.

These and other objects of the present invention will become apparent from the description hereinafter.

SUMMARY OF THE INVENTION

The present invention provides an adhesive tape comprising a water impermeable, gas permeable tape substrate, a pressure-sensitive adhesive layer provided on one side of the tape substrate, and a porous sheet provided on a portion of the pressure-sensitive adhesive layer, the porous sheet being capable of expanding to have an apparent density of 0.01 to 0.20 g/cm$^3$ when absorbing water to saturation.

According to a preferred embodiment of the present invention, the tape substrate has a water vapor transmission rate of at least 400 g/m$^2$·24 hrs.

According to another preferred embodiment of the present invention, the porous sheet is a cellulosic porous sheet produced by mechanically compressing a cellulosic sponge.

According to still another preferred embodiment of the present invention, the porous sheet is a polyurethane porous sheet produced by thermocompression-molding a hydrophilic polyurethane sponge.

DETAILED DESCRIPTION

The adhesive tape of the present invention uses a water impermeable, gas permeable sheet as a tape substrate. Accordingly, when the adhesive tape is applied on some portion of a body, water does not enter the interface between the tape substrate and the skin through the tape substrate due to the water impermeability of the tape substrate. Further, even when the skin on which the adhesive tape is being applied perspires, the resulting water vapor escapes outside through the tape substrate due to the gas permeability of the tape substrate, so that water is not accumulated between the adhesive tape and the skin.

The adhesive tape of the present invention uses as a pad a porous sheet which is expandable upon absorbing water. Accordingly, when the adhesive tape is applied onto a wound, the pad absorbs blood from the wound to expand. Since the tape substrate is firmly adhered to the skin, the expansion force of the pad effectively presses against the wound, resulting in an enhanced hemostasis effect.

The present invention will be explained in detail.

Figure 1:
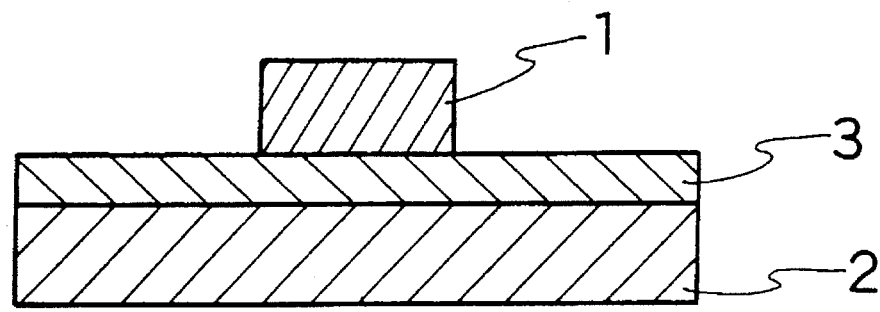
FIG. 1 is a sectional view showing an example of the adhesive tape according to the present invention.

FIG. 1 is a sectional view showing an example of the adhesive tape of the present invention. In FIG. 1, reference numeral 1 denotes a porous sheet, reference numeral 2 denotes a tape substrate and reference numeral 3 denotes a pressure-sensitive adhesive layer 3.

The adhesive tape of this example comprises a tape substrate 2, a pressure-sensitive adhesive layer 3 provided on one side of the tape substrate 2, and a porous sheet 1 adhered on a portion of the pressure-sensitive adhesive layer 3.

The tape substrate 2 is a water impermeable, gas permeable sheet which transmits gases such as water vapor but prevents the entrance of liquids such as water.

Examples of structures of such sheet are a single layer sheet having a porous structure made of one or more materials such as fluororesin, silicone resin, polyamino acid resin and polyurethane resin; a coated sheet produced by coating one or both sides of a base sheet, such as nonwoven fabric, woven fabric or knit fabric, with one or more resins such as polyurethane resin, polyamino acid resin, fluororesin and silicone resin, and laminated sheet produced by laminating on one or both sides of the foregoing base sheet a porous sheet made of one or more resins such as polyurethane resin, polyamino acid resin, fluororesin and silicone resin, as described in Japanese Examined Patent Publication No. 39 140/1994; and further a sheet produced by film-forming a mixture containing one or more resins such as polyurethane resin, polyamino acid resin, fluororesin and silicone resin, with one or more other resins such as polyvinyl chloride, polyethylene and polypropylene, as described in Japanese Unexamined Patent Publication No. 115239/1990.

The tape substrate 2 preferably has a water vapor transmission rate (measured in an atmosphere of 40° C. and 70% RH by Pain Cup method) of at least 400 g/m²·24 hrs. When the water vapor transmission rate is smaller than 400 g/m²·24 hrs, water vapor generated between the skin and the adhesive tape is prone to be condensed into water, resulting in easy peeling of the adhesive tape.

From the viewpoint of mechanical strength and the like, the tape substrate 2 preferably has a thickness of from 10 to 500 μm, more preferably from 30 to 200 μm.

One side of the tape substrate 2 is coated with a pressure-sensitive adhesive layer 3, by which the adhesive tape can be adhered to a skin. Examples of pressure-sensitive adhesives for the adhesive layer 3 are acrylic resin type and polyvinyl ether type.

A porous sheet 1 is adhered to some portion, preferably a central portion of the pressure-sensitive adhesive layer 3. The porous sheet 1 may be adhered directly to the surface of the pressure-sensitive adhesive layer 3. Alternatively the porous sheet 1 may be adhered to the surface of the pressure-sensitive adhesive layer 3 by use of an adhesive.

When the adhesive tape is applied onto a skin having a wound, the porous sheet 1 is pressed against the wound and hermetically sealed by the pressure-sensitive adhesive layer 3 adhered to the skin.

Usable as the porous sheet 1 are those which are capable of expanding to have an apparent density of 0.01 to 0.20 g/cm³ under a free expansion condition when absorbing water to saturation. Herein, the apparent density is defined as a physical value obtained by dividing the weight of a dried porous sheet by the volume of the porous sheet which is allowed to absorb water to saturation. When the apparent density of the porous sheet upon absorbing water to saturation is smaller than 0.01 g/cm³, the porous sheet expands excessively so that the adhesive tape adhered to the skin is partially peeled off from the skin to invite a danger that microorganisms enter the inside from the outside. When the apparent density of the porous sheet when absorbing water to saturation is larger than 0.20 g/cm³, the force of pressing against a wound reduced, resulting in a reduced hemostasis effect.

Examples of the porous sheet 1 capable of expanding to have an apparent density of 0.01 to 0.20 g/cm³ when absorbing water to saturation are a cellulosic porous sheet produced by mechanically compressing a cellulosic sponge, as described in Japanese Examined Patent Publication No. 79662/1992, and a polyurethane porous sheet produced by thermocompression-molding a hyrophilic polyurethane sponge, as described in Japanese Unexamined Patent Publication No. 31825/1994. The aforesaid cellulosic sponge can be produced by expansion-molding a mixture of viscose and a foaming agent, and optionally, a reinforcing cut fiber such as rayon, cotton or bast fiber, as described in Japanese Unexamined Patent Publication No. 65045/1977.

The above-mentioned porous sheets have the following characteristic properties: The porous sheet absorbs water at an extremely high speed. That is, the water absorption rate of the porous sheet is not more than 1.3 seconds/cm. Herein, the water absorption rate is measured as follows: A long specimen having a width of 1 cm is dipped at one end thereof in water for 10 seconds, and the length that water rises in the specimen during the time was determined. The water absorption rate (second/cm) was calculated from the length and the time. Further, the porous sheet can absorb a large amount of water. That is, the water absorbing capacity of the porous sheet is not smaller than 0.5 g water/g dry porous sheet. Herein, the water absorbing capacity is a value measured with respect to a specimen prepared by the method wherein a dried porous sheet is allowed to absorb water to saturation and then subjected to dewatering operation using a centrifuge for 3 minutes. The porous sheet can expand in a volume expansion ratio of 5 to 25 when absorbing water to saturation. Further, when the adhesive tape having the porous sheet is firmly adhered to a skin with a wound and the porous sheet absorbs blood, the porous sheet produces such an expansion force that it can expand against the repulsive force of the skin, thereby strongly pressing against the wound.

The thickness of the porous sheet is preferably from 0.2 to 5 mm, more preferably from 0.5 to 2 mm from the viewpoint of ensuring a sufficient expansion force. The size of the porous sheet is not particularly limited. Usually the porous sheet has a size of 5 to 100 mm×10 to 150 mm.

The present invention will be more fully described by way of Examples. It is to be understood that the present invention is not limited to the Examples, and various changes and modifications may be made in the invention without departing from the spirit and scope thereof.

EXAMPLE 1

A 150 μm-thick water impermeable, gas permeable sheet made of a fluororesin, available under the commercial name "PERME-AID" from Nitto Denko Corporation (water vapor transmission rate: 745 g/m²·24 hrs) was cut to give a piece having a size of 80 mm×20 mm as a tape substrate.

A 1.8 mm-thick porous cellulosic sheet (apparent density when absorbing water to saturation: 0.034 g/cm³) produced by mechanically compressing a cellulosic sponge was cut to give a piece having a size of 10 mm×10 mm as a pad. The cellulosic sponge was produced by adding to a viscose solution a cotton in an amount of 25% by weight based on the amount of the viscose (on a solid basis), and a foaming agent, and expansion-molding the resulting mixture.

The whole surface of one side of the tape substrate was coated with an acrylic resin pressure-sensitive adhesive to an adhesive layer having a thickness of 30 μm. The pad was adhered to a central portion of the adhesive layer to give an adhesive tape.

The adhesive tape was applied to the inner surface of a forearm of a user to determine whether the adhesive tape was peeled off from the skin. The results are shown in Table 1. Evaluation was conducted as follows:

○ . . . The adhesive tape was not peeled off from the skin even when taking a bath.

Δ . . . The adhesive tape was peeled off from the skin when taking a bath.

X . . . The adhesive tape was peeled off from the skin in a day.

Comparative Example 1

A 150 μm-thick soft polyvinyl chloride sheet (water vapor transmission rate: 242 g/m²·24 hrs) was cut to give a piece having a size of 80 mm×20 mm as a tape substrate.

The same procedures as Example 1 except that this tape substrate was used instead of the tape substrate used in Example 1 were repeated to give an adhesive tape.

The adhesive tape was applied to the inner surface of a forearm of a user to determine whether the adhesive tape was peeled off from the skin, in the same manner as in Example 1. The results are shown in Table 1.

Comparative Example 2

A 200 μm-thick plain weave cotton fabric was cut to give a piece having a size of 80 mm×20 mm as a tape substrate.

The same procedures as Example 1 except that this tape substrate was used instead of the tape substrate used in Example 1 were repeated to give an adhesive tape.

The adhesive tape was applied to the inner surface of a forearm of a user to determine whether the adhesive tape was peeled off from the skin, in the same manner as in Example 1. The results are shown in Table 1.

TABLE 1

|  | Evaluation |
| --- | --- |
| Ex. 1 | ○ |
| Com. Ex. 1 | X |
| Com. Ex. 2 | Δ |

As is apparent from Table 1, the adhesive tape of Example 1 is not peeled off from the skin after the user takes a bath. However, the adhesive tape of Comparative Example 1 is peeled off from the skin after the user takes a bath and the adhesive tape of Comparative Example 2 is peeled off from the skin in a day.

EXAMPLE 2

Figure 2:
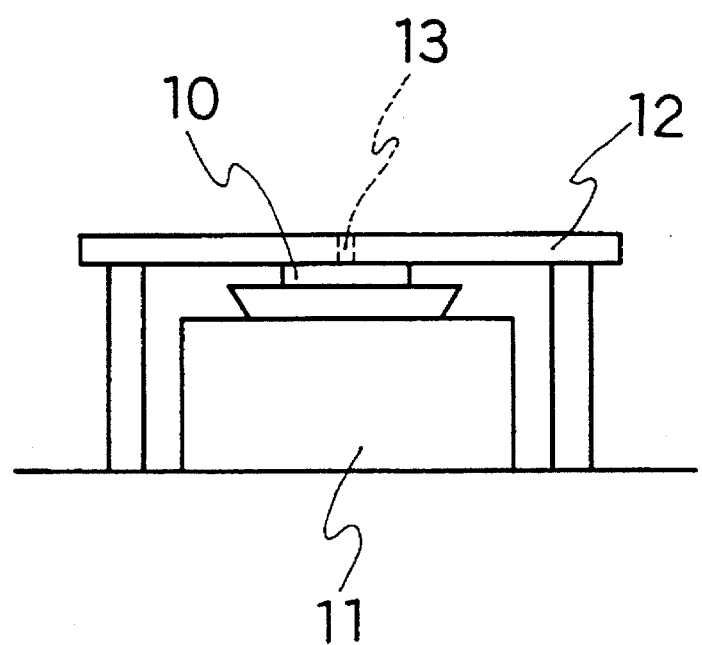
FIG. 2 is an explanatory view showing an apparatus for measuring the expansion force of the porous sheet used in the present invention.

The apparatus as shown in FIG. 2 was used.

The same cellulosic porous sheet except that the thickness thereof was 2.2 mm was cut to give a test piece having a size of 10 mm×10 min.

The test piece 10 was placed on the pan of an electronic scales 11 and a bridge 12 made of iron was placed over the electronic scales 11 so that the upper surface of the test piece 10 was brought into contact with the lower surface of the horizontal member of the bridge 12, and the test piece 10 was located at the position of the bridge 12 where a small opening 13 was provided. After the electronic scales 11 was brought to a zero reading, water was dropped on the cellulosic porous sheet through the small opening 13.

The scale was read as the mount of water dropped was increased. The results are shown in Table 2.

Comparative Example 3

A 10 mm×10 mm piece of a 2.3 mm-thick cotton nonwoven fabric was placed on the electronic scales 11 in the same manner as in Example 2 and water was dropped on the cotton nonwoven fabric through the small opening 13 in the same manner as in Example 2 and the scale was read as the amount of water dropped was increased. The results are shown in Table 2.

TABLE 2

| Total amount of water dropped (ml) | Read scale (g) | |
| --- | --- | --- |
| | Ex. 2 | Com. Ex. 3 |
| 0.01 | 33.8 | 2.3 |
| 0.02 | 70.6 | 1.9 |
| 0.03 | 91.6 | 2.0 |
| 0.04 | 100.4 | 2.0 |
| 0.05 | 103.2 | 1.9 |
| 0.06 | 103.6 | 2.0 |
| 0.07 | 103.5 | 2.0 |

As is apparent from Table 2, in the case of Example 2, the pressure (the expansion force of the cellulosic porous sheet) largely increases as increasing amount of water dropped until the total amount of water dropped becomes about 0.05 ml, which reveals that the cellulosic porous sheet produces a great pressure when it absorbs water. In contrast thereto, in the case of Comparative Example 3, a slight increase in pressure is observed until the total amount of water dropped becomes about 0.01 ml, and the pressure rather decreases as the total amount of water dropped further increases.

In addition to the materials and ingredients used in Examples, other materials and ingredients can be used in Examples as set forth in the specification to obtain substantially the same results.

The adhesive tape of the present invention prevents the accumulation of perspiration between the adhesive tape and the skin of a user on which the adhesive tape is being applied and, hence, is not readily peeled off from the skin. In particular, even when a user takes a bath immediately after the user applies the adhesive tape of the present invention to a bleeding wound on its own skin, the adhesive tape is not peeled off from the skin. Accordingly, a patient who is being subjected to dialysis treatment can take a bath immediately after the adhesive tape of the present invention is applied to the portion of the patient where a needle for dialysis is extracted after termination of a dialysis operation. Thus, the portion where the needle is extracted sanitarily treated. Further, when the adhesive tape of the present invention is applied to a bleeding wound, the porous sheet expands upon absorbing the blood to press against the wound, resulting in an enhanced hemostasis effect.

What is claimed is:

1. An adhesive tape comprising a water impermeable, gas permeable tape substrate, a pressure-sensitive adhesive layer provided on one side of the tape substrate, and a porous sheet provided on a portion of the pressure-sensitive adhesive layer, the porous sheet being capable of expanding to have an apparent density of 0.01 to 0.20 g/cm$^3$ when absorbing water to saturation.

2. The adhesive tape of claim 1, wherein the tape substrate has a water vapor transmission rate of at least 400 g/m$^2$·24 hrs.

3. The adhesive tape of claim 1, wherein the porous sheet is a cellulosic porous sheet produced by mechanically compressing a cellulosic sponge.

4. The adhesive tape of claim 1, wherein the porous sheet is a polyurethane porous sheet produced by thermocompression-molding a hydrophilic polyurethane sponge.

* * * * *